US012728146B2

(12) United States Patent
Bezzarga

(10) Patent No.: US 12,728,146 B2
(45) Date of Patent: Sep. 8, 2026

(54) THERAPEUTIC COMPOSITION BASED ON ESSENTIAL OILS AT LOW DOSES

(71) Applicant: Mounir Bezzarga, Hammam-Lif (TN)

(72) Inventor: Mounir Bezzarga, Hammam-Lif (TN)

( * ) Notice: Subject to any disclaimer, the term of this patent is extended or adjusted under 35 U.S.C. 154(b) by 542 days.

(21) Appl. No.: 18/250,641

(22) PCT Filed: Nov. 3, 2021

(86) PCT No.: PCT/IB2021/060180

§ 371 (c)(1),
(2) Date: Apr. 26, 2023

(87) PCT Pub. No.: WO2022/097042

PCT Pub. Date: May 12, 2022

(65) Prior Publication Data

US 2024/0293495 A1 Sep. 5, 2024

(30) Foreign Application Priority Data

Nov. 3, 2020 (TN) .............................. TN2020/0211

(51) Int. Cl.

| | |
|---|---|
| ***A61K 36/54*** | (2006.01) |
| ***A61K 9/08*** | (2006.01) |
| ***A61K 31/05*** | (2006.01) |
| ***A61K 31/125*** | (2006.01) |
| ***A61K 36/534*** | (2006.01) |
| ***A61K 36/61*** | (2006.01) |
| ***A61K 47/44*** | (2017.01) |
| ***A61P 31/14*** | (2006.01) |

(52) U.S. Cl.

CPC ................ *A61K 36/54* (2013.01); *A61K 9/08* (2013.01); *A61K 31/05* (2013.01); *A61K 31/125* (2013.01); *A61K 36/534* (2013.01); *A61K 36/61* (2013.01); *A61K 47/44* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 7,048,953 B2 | 5/2006 | Vail, III et al. | |
| 2004/0009245 A1* | 1/2004 | Vail, III ................. | A61M 11/06 424/742 |

OTHER PUBLICATIONS

Horvath, G., Acs, K., Essential oils in the treatment of respiratory tract diseases highlighting their role in bacterial infections and their anti-inflammatory action: a review, Flavour and Fragrance Journal, vol. 30, Sep. 2015, 331-341 (Year: 2015).*

Lahsissene, H., et al., Usages therapeutiques traditionnels des plantes medicinales dans le Maroc occidental: cas de la region de Zaer, Phytotherapie; de la recherche a la pratique, vol. 8, No. 4, Jul. 22, 2010, 210-217 (Year: 2010).*

Mimica-Dukic, N., et al., Antimicrobial and antioxidant activities of three Mentha species essential oils, (2003) URL:https://www.thieme-connect.com/products/ejournals/pdf/10.1055/s-2003-39704.pdf XP055890853 (Year: 2003).*

Anonymous, "Etudes cliniques", Jul. 15, 2021 (Jul. 15, 2021), Retrieved from the Internet: URL:http://193.95.84.4/webdpm1/Francais/aspec/liste_ec.asp XP055890621 [retrieved on Feb. 11, 2022].

Anonymous, "L'huile de sesame, un trésor de douceur et d'antioxydants", Feb. 5, 2020 (Feb. 5, 2020), Retrieved from the Internet: URL:https://www.rtbf.be/article/l-huile-de-sesame-un-tresor-de-douceur-et-d-antioxydants-10425324 XP055890854 [retrieved on Feb. 11, 2022].

Anonymous, "Oregano Oil", GNPD19 Mar. 2020 (Mar. 19, 2020), Database accession No. 7443753, Retrieved from the Internet: URL:MINTEL XP055890855.

Asif et al., "COVID-19 and therapy with essential oils having antiviral, anti-inflammatory, and immunomodulatory properties", Inflammopharmacology, vol. 28, No. 5, Aug. 14, 2020 (Aug. 14, 2020), p. 1153-1161, XP037376410 DOI: 10.1007/S10787-020-00744-0 external link ISSN:0925-4692.

Da Silva, Joyce Kelly R et al., "Essential Oils as Antiviral Agents, Potential of Essential Oils to Treat SARS-CoV-2 Infection: An In-Silico Investigation", International Journal of Molecular Sciences, vol. 21, No. 10, May 12, 2020 (May 12, 2020, p. 1-35, XP055787017 DOI: 10.3390/ijms21103426 external link ISSN:1661-6596.

Horváth et al., "Essential oils in the treatment of respiratory tract diseases highlighting their role in bacterial infections and their anti-inflammatory action: a review : Essential oils in the treatment of respiratory tract diseases", Flavour and Fragrance Journal., vol. 30, No. 5, May 26, 2015 (May 26, 2015), p. 331-341, XP055391769 DOI: 10.1002/ffj.3252 external link ISSN:0882-5734.

International Search Report dated Mar. 1, 2022 from PCT Application No. PCT/IB2021/060180.

Lahsissene H et al, "Usages thérapeutiques traditionnels des plantes médicinales dans le Maroc occidental: cas de la region de Zaer", Phytotherapie ; De La Recherche À La Pratique, Springer-Verlag, PA, vol. 8, No. 4, Jul. 22, 2010 (Jul. 22, 2010), p. 210-217, XP019809650ISSN:1765-2847.

Mimica-Dukic, Neda, "Antimicrobial and Antioxidant Activities of Three Mentha Species Essential Oils", Jan. 1, 2003 (Jan. 1, 2003), Retrieved from the Internet: URL:https://www.thieme-connect.com/products/ejournals/pdf/10.1055/s-2003-39704.pdf XP055890853 [retrieved on Feb. 11, 2022].

(Continued)

*Primary Examiner* — H. Sarah Park

(74) *Attorney, Agent, or Firm* — INNOVATION CAPITAL LAW GROUP, LLP; Vic Lin

(57) ABSTRACT

The invention consists in the use of a composition of essential oils at low doses for treating influenza, acute bronchitis, inflammation and other infections of the respiratory tract. This composition is a mixture of low doses of natural substances stimulating immunity. The immunity stimulating activity is obtained by synergistic effect between essential oils at low doses used with weighting.

16 Claims, No Drawings

(56) References Cited

OTHER PUBLICATIONS

Sepahvand, Asghar et al., "Phytotherapy in Aspergillus: An overview of the most important medicinal plants affecting Aspergillus", Jan. 1, 2016 (Jan. 1, 2016), Retrieved from the Internet: URL:https://sphinxsai.com/2016/ph_vol9_no6/1/(274-284)V9N6PT.pdf XP055890851 [retrieved on Feb. 11, 2022].

Tafrihi, Majid et al., "The Wonderful Activities of the Genus Mentha: Not Only Antioxidant Properties", Molecules, vol. 26, No. 4, Feb. 20, 2021 (Feb. 20, 2021), p. 1118, XP055890742 DOI: 10.3390/molecules26041118 external link.

Winska, Katarzyna et al, "Essential Oils as Antimicrobial Agents—Myth or Real Alternative?", Sep. 5, 2016 (Sep. 5, 2016), vol. 24, No. 11, p. 2130, Retrieved from the Internet: URL:https://www.ncbi.nlm.nih.gov/pmc/articles/PMC6612361/pdf/molecules-24-02130.pdf XP055800965.

* cited by examiner

THERAPEUTIC COMPOSITION BASED ON ESSENTIAL OILS AT LOW DOSES

The present invention relates to a composition of essential oils at low doses and the use thereof for treating influenza, acute bronchitis, inflammation and other respiratory tract infections.

The pathogen agents responsible for respiratory tract infections are most of the time viruses. Infections can affect the upper or lower part of the respiratory tract, although the latter area is more rarely affected but usually more severely. Thus, upper respiratory tract infections affect the nose, sinuses, pharynx and larynx. These infections include influenza and the common cold, for the most common of them. Lower respiratory tract infections affect the trachea, airways and lungs and are more common in children. Pneumonia and bronchitis are the most common forms of lower respiratory tract infections.

Thus, some viruses, such as the influenza virus, can cause infections in the upper and lower respiratory tract.

Viruses spread mainly through nasal secretions from infected people, which contaminate their hands and which are then transmitted, for example, to the mouths of healthy people. Common cold symptoms are mild and usually disappear within 4 to 10 days.

In this context, the coronavirus 2 pandemic (Sars-CoV-2) time period required a rapid and effective healthcare response. However, until this time period, developing and market launching effective and safe antiviral products have always proven to be long (possibly stretching over several years or even decades) or even tedious processes. Thus, essential oils, known for a long time to contain antiviral agents against certain pathogenic viruses, have appeared as interesting candidate active agents in the preparation of a product for fighting respiratory tract infections and in particular an infection relating to Sars-CoV-2.

The invention relates, in its broadest sense, to a therapeutic composition comprising a mixture of at least four essential oils for the use thereof in treating at least one respiratory infection, preferably selected from the list consisting of a spearmint essential oil, menthol, a water mint essential oil, a clove essential oil, a peppermint essential oil, a pennyroyal essential oil, a eucalyptus essential oil, a cinnamon essential oil, in particular a cinnamon bark essential oil, a cajuput essential oil, and camphor.

In addition, the invention relates to a therapeutic composition in the form of an ampoule with a volume of five milliliters to ten milliliters comprising essential oils at low doses and an excipient comprising at least one edible vegetable oil.

The invention also relates to a therapeutic composition in the form of an ampoule with a volume of five milliliters to ten milliliters comprising essential oils at low doses and an excipient comprising at least one edible vegetable oil, for its oral use for treating influenza, acute bronchitis and other respiratory infections.

"Essential oil" is generally understood as a liquid extract obtained (generally by distillation, for example using steam) from a plant and which typically concentrates the active ingredients therefrom. In the context of the present invention, this expression also encompasses the active ingredients of these plants obtained synthetically. For example, the menthol is typically obtained by extracting a mint distillate (such as peppermint), but can also be synthesized.

"Respiratory infection" is understood in the context of the present invention as an infection reaching the structures of the respiratory system, namely the nose, the ears, the throat, the larynx, the trachea, the bronchi or the lungs. The pathogens responsible for respiratory tract infections are mostly viruses (i.e., those infections are therefore viral respiratory infections).

"At low doses" is understood in the context of the present invention as meaning doses that do not cause a toxic effect on the human body.

The present invention therefore relates to the composition described above and the uses thereof as described above.

Preferably, the composition can also be characterized in that:

- the essential oil mixture includes at least five constituents selected from the list consisting of a spearmint essential oil, menthol, a water mint essential oil, a clove essential oil, a peppermint essential oil, a pennyroyal essential oil, a eucalyptus essential oil, a cinnamon essential oil, in particular a cinnamon bark essential oil, a cajuput essential oil, and camphor;
- the essential oil mixture includes all the constituents selected from the list consisting of a spearmint essential oil, menthol (crystals), a water mint essential oil, a clove essential oil, a peppermint essential oil, a pennyroyal essential oil, a eucalyptus essential oil, a cinnamon essential oil, in particular a cinnamon bark essential oil, a cajuput essential oil, and camphor;
- said composition is intended for oral administration;
- said composition further comprises at least one edible vegetable oil as an excipient;
- the excipient is selected from sesame oil, olive oil or a mixture thereof;
- said composition comprises between 4 grams and 9 grams of excipient;
- said composition is in the form of an ampoule, such as an ampoule with a volume of five milliliters to ten milliliters;
- said composition comprises between 0.62 grams and 1.0 grams of a mixture of essential oils;
- said composition includes between 0.04 and 0.08 grams of spearmint essential oil, between 0.05 and 0.09 grams of menthol, between 0.03 and 0.07 grams of a water mint essential oil, between 0.02 and 0.06 grams of a clove essential oil, between 0.03 and 0.07 grams of a peppermint essential oil, between 0.02 and 0.06 grams of a pennyroyal essential oil, between 0.12 and 0.16 grams of a eucalyptus essential oil, between 0.02 and 0.06 grams of a cinnamon essential oil, between 0.04 and 0.08 grams of a cajuput essential oil, and/or between 0.23 and 0.27 grams of Camphor, and optionally between 4 and 9 grams of edible sesame vegetable oil as an excipient;
- said composition includes 0.08 grams of a spearmint essential oil, 0.09 grams of menthol, 0.07 grams of a water mint essential oil, 0.06 grams of a clove essential oil, 0.07 grams of a peppermint essential oil, 0.06 grams of a pennyroyal essential oil, 0.16 grams of a eucalyptus essential oil, 0.06 grams of a cinnamon essential oil, 0.08 grams of a cajuput essential oil, and/or 0.27 grams of Camphor and optionally 9 grams of edible vegetable oil as an excipient;
- the excipient is selected from sesame oil, olive oil or a mixture thereof; and/or
- the respiratory infection is selected from influenza, common cold, bronchitis, such as acute bronchitis, a pneumopathy, such as viral pneumonia or a Sars-CoV-2 related pneumopathy.

Preferably, the mixture of essential oils includes at least six constituents selected from the list consisting of a spearmint essential oil, menthol, a water mint essential oil, a clove essential oil, a peppermint essential oil, a pennyroyal essential oil, a eucalyptus essential oil, a cinnamon essential oil, a cajuput essential oil, and camphor.

More preferably, the essential oil mixture includes at least seven constituents selected from the list consisting of a spearmint essential oil, menthol, a water mint essential oil, a clove essential oil, a peppermint essential oil, a pennyroyal essential oil, a eucalyptus essential oil, a cinnamon essential oil, in particular a cinnamon bark essential oil, a cajuput essential oil, and camphor.

More preferably, the mixture of essential oils includes at least eight constituents selected from the list consisting of a spearmint essential oil, menthol, a water mint essential oil, a clove essential oil, a peppermint essential oil, a pennyroyal essential oil, a eucalyptus essential oil, a cinnamon essential oil, a cajuput essential oil, and camphor.

Most preferably, the mixture of essential oils includes at least nine constituents selected from the list consisting of a spearmint essential oil, menthol, a water mint essential oil, a clove essential oil, a peppermint essential oil, a pennyroyal essential oil, a eucalyptus essential oil, a cinnamon essential oil, a cajuput essential oil, and camphor.

In one embodiment, said composition is intended for oral administration.

Thus, a composition according to the present invention can take any form (solid or liquid) suitable for such oral administration, such as in the form of tablets, pill (in French "gélule"), capsules, powder, syrup, or drink, optionally by means of galenic form or a device providing extended and/or delayed release, such as a dissolution retardant coating. For this type of formulation providing extended and/or delayed release, an agent such as cellulose, carbonates or starch is advantageously used.

Indeed, being ab initia in liquid form, the composition according to the present invention, can be absorbed on any solid supporting substrate allowing its incorporation into a solid, or pasty, formulation.

Preferably, the composition according to the present invention is provided as a liquid formulation.

Preferably, the composition according to the present invention is suitable for being formulated in the form of an ampoule.

Preferably, the composition according to the present invention is suitable for being formulated in the form of an ampoule with a volume of five milliliters to ten milliliters.

In a particular embodiment, the edible vegetable oil as an excipient can be a mixture of sesame oil and olive oil. The proportions of sesame oil:olive oil in the mixture may vary from 1:10 to 10:1 in weight, respectively.

Preferably, the proportions of sesame oil:olive oil in the mixture can vary from 1:8 to 8:1 by weight, from 1:6 to 6:1 by weight, from 1:4 to 4:1 by weight, from 1:2 to 2:1 by weight, or even 1:1 by weight respectively.

In addition, the composition according to the present invention may comprise between 5 grams and 8 grams of excipient, preferably between 6 grams and 7 grams, or even between 8 grams and 9 grams In addition, the composition according to the present invention may comprise between 0.70 grams and 0.95 grams of a mixture of essential oils, preferably between 0.75 grams and 0.90 grams, or even between 0.80 grams and 0.85 grams of a mixture of essential oils.

Preferably, the sum of the masses of excipient(s) (such as sesame oil) and the mixture of essential oils is between 5.62 grams and 10 grams, preferably between 6 grams and 9 grams, between 7 grams and 8 grams or even 10 grams.

Thus the proportions of the different essential oils in the composition according to the present invention can be reduced to a ratio between the minimum content in each essential oil and the total weight of the composition:

- between 0.4% and 1.42% by weight ratio of a spearmint essential oil relative to the total weight of the composition;
- between 0.50% and 1.60% by weight ratio menthol relative to the total weight of the composition;
- between 0.30%% and 1.24% by weight ratio of a water mint essential oil relative to the total weight of the composition,
- between 0.20% and 1.07% by weight ratio of a clove essential oil relative to the total weight of the composition,
- between 0.30% and 1.25% by weight ratio of a peppermint essential oil relative to the total weight of the composition,
- between 0.20% and 1.07% by weight ratio of a pennyroyal essential oil relative to the total weight of the composition,
- between 1.20% and 2.85% by weight ratio of a eucalyptus essential oil relative to the total weight of the composition,
- between 0.20% and 1.07% by weight ratio of a cinnamon essential oil relative to the total weight of the composition,
- between 0.40% and 1.42% by weight ratio of a cajuput essential oil relative to the total weight of the composition, and/or
- between 2.30% and 4.81% by weight ratio Camphor relative to the total weight of the composition;

Preferably, the spearmint essential oil comprises, in the context of the present invention, carvone and limonene, for example 40.8% carvone and 20.8% limonene.

Preferably, the menthol includes in the context of the present invention menthol, for example 100% menthol.

Preferably, the water mint essential oil comprises, in the context of the present invention, limonene, menthofuran, ocimene and beta-caryophyllene, for example 12.06% limonene, 51.26% menthofuran, 8.1% ocimene and 2.92% beta-caryophyllene.

Preferably, the clove essential oil comprises, in the context of the present invention, eugenol, beta-caryophyllene, alpha-humulene, acetyleugenol, for example 76, 8% eugenol, 17.4% beta-caryophyllene, 2.1% alpha-humulene, 1.2% acetyleugenol.

Preferably, the peppermint essential oil comprises, in the context of the present invention, menthol, menthone, 1,8-cineole, neomenthol and menthyl acetate, for example 39.81% menthol, 19.55% menthone, 5.81%1,8-cineole, 8.83% neomenthol and 8.64% menthyl acetate.

Preferably, the pennyroyal essential oil comprises, in the context of the present invention, menthol, pulegone, neomenthol, for example 35.9% menthol, 23.2% pulegone, 9.2% neomenthol.

Preferably, the eucalyptus essential oil comprises in the context of the present invention limonene, alpha-terpineol, alpha-terpinyl acetate, alpha-pinene, for example 80.51% limonene, 8.6% alpha-terpineol, 6.07% alpha-terpinyl acetate, 3.01% alpha-pinene.

Preferably, the cinnamon essential oil comprises in the context of the present invention eugenol, alpha-pinene, cinnamaldehyde, cinnamyl acetate, linalool, for example 5.8% eugenol, 2.6% alpha-pinene, 76.8% cinnamaldehyde, 3.1% cinnamyl acetate, 2.4% linalool.

Preferably, the cajuput essential oil comprises, in the context of the present invention, 1,8-cineole, viridiflorol, for example 21.3%1,8-cineole, 28.2% viridiflorol.

Preferably, camphor comprises, in the context of the present invention, 1,8-cineole, alpha-terpineol, camphor and safrole, for example 30.02%1,8-cineole, 5.22% alpha-terpineol, 36.61% camphor and 5.15% safrole.

Preferably, the sesame oil comprises, in the context of the present invention, linoleic acid, oleic acid, palmitic acid and stearic acid, for example 41% linoleic acid, 39% oleic acid, 8% palmitic acid and 5% stearic acid.

In addition, the object of the present invention relates more particularly to a therapeutic composition in the form of an ampoule with a volume of five milliliters to ten milliliters comprising essential oils at low doses and an excipient comprising at least one edible vegetable oil.

Preferably, the composition can also be characterized in that:

the excipient is sesame oil or olive oil;

the mixture of essential oils contains between two hundred fifty milligrams and one gram, preferably between 0.6 grams and 1.0 gram active substances (the essential oils with the menthol).

the mixture of essential oils includes a spearmint essential oil, menthol, a water mint essential oil, a clove essential oil, a peppermint essential oil, a pennyroyal essential oil, a eucalyptus essential oil, a cinnamon essential oil, in particular a cinnamon bark essential oil, a cajuput essential oil, and camphor;

the essential oil mixture includes between 0.04 and 0.08 grams of a spearmint essential oil, between 0.05 and 0.09 grams of menthol, between 0.03 and 0.07 grams of a water mint essential oil, between 0.02 and 0.06 grams of a clove essential oil, between 0.03 and 0.07 grams of a peppermint essential oil, between 0.02 and 0.06 grams of a pennyroyal essential oil, between 0.12 and 0.16 grams of a eucalyptus essential oil, between 0.02 and 0.06 grams of a cinnamon essential oil, in particular a cinnamon bark essential oil, between 0.04 and 0.08 grams of a cajuput essential oil, between 0.23 and 0.27 grams of Camphor; and/or said composition includes 0.08 grams of a spearmint essential oil, 0.09 grams of menthol, 0.07 grams of a water mint essential oil, 0.06 grams of a clove essential oil, 0.07 grams of a peppermint essential oil, 0.06 grams of a pennyroyal essential oil, 0.16 grams of a eucalyptus essential oil, 0.06 grams of a cinnamon essential oil, 0.08 grams of a cajuput essential oil, 0.27 grams of Camphor and 9 grams of sesame oil.

The object of the present invention further relates to a therapeutic composition as described above, for its oral use for treating influenza, acute bronchitis and other respiratory infections.

More particularly, the invention relates to a stimulant composed of an average dose of one gram distributed by weighting low doses of essential oils in a sesame oil excipient to facilitate their absorption. The benefits of the content of these oils in active substances can be summarized as follows:

1) Spearmint Essential Oil: Treatment of respiratory tract infections;
2) Menthol: Anti-inflammatory and antiviral effect.
3) Water Mint Essential Oil: Refreshing properties;
4) Clove Essential Oil: Anti-infectious, antiviral, antibacterial and immune stimulant effects;
5) Peppermint Essential Oil: Effects against nausea, migraines, headaches and rheumatic pains, Refreshing and eases digestion;
6) Pennyroyal Essential Oil: Participates in proper liver function;
7) Eucalyptus Essential Oil: Effective role against irritation and dryness in relieving sinusitis and easing wet cough;
8) Cinnamon Essential Oil, in particular a cinnamon bark essential oil: Anti-infectious, bactericidal and virucidal actions. It is an immune system stimulant;
9) Cajuput Oil, in particular Cajuput Essential Oil: protects the nervous system and it is an immune stimulant, anti-inflammatory and antioxidant recommended during epidemics;
10) Camphor: Has anti-inflammatory, antiseptic and anesthetic properties and it is an immune stimulant and antioxidant recommended in times of epidemics;
11) Sesame Oil: excipient, and facilitates absorption, and is rich in vitamins E and B, magnesium and zinc.

A composition is formed from a mixture of low doses of essential oils in a natural substance excipient to stimulate immunity. The total share of essential oils in this composition is one gram or less than one gram and that of the sesame oil excipient is between four and nine grams. This composition is detailed in the following table.

TABLE 1 mixtures of essential oils covered

| COMPOSITION[ ] | IN PARTICULAR LATIN NAME | GRAMS |
|---|---|---|
| SPEARMINT ESSENTIAL OIL | Mentha spicata | 0.04 to 0.08 |
| MENTHOL | | 0.05 to 0.09 |
| WATER MINT ESSENTIAL OIL | Menthae arvensis aetheroleum | 0.03 to 0.07 |
| CLOVE ESSENTIAL OIL | Syzygium aromaticum | 0.02 to 0.06 |
| PEPPERMINT ESSENTIAL OIL | Mentha piperita | 0.03 to 0.07 |
| PENNYROYAL ESSENTIAL OIL | Mentha poulegium | 0.02 to 0.06 |
| EUCALYPTUS ESSENTIAL OIL | Eucalyptus globulus | 0.12 to 0.16 |
| CINNAMON (BARK) ESSENTIAL OIL | Cinnamomum verum | 0.02 to 0.06 |
| ESSENTIAL OIL | Melaleuca leucadendron cajuputii | 0.04 to 0.08 |
| CAMPHOR, FOR EXAMPLE CAMPHOR CRYSTALS OR ESSENTIAL OIL | Cinnamomum camphora | 0.23 to 0.27 |
| QSP SESAME OIL | Sesama | 4 to 9 |

As regards the use, preferably, the dosage and the galenic form of the composition according to the present invention is adapted to the pathology and to the treated patient.

For example, the dosage may consist of a single dose, for example for oral administration, in the case of influenza, acute bronchitis and other respiratory infections.

Alternatively, the dosage may consist of a recurring daily, weekly or monthly intake of a single dose, for example orally, in the event of influenza, acute bronchitis and other respiratory infections.

Preferably, the administered formulation quantity is adapted to the weight of the patient.

In a particular embodiment, the composition according to the present invention is administered preventively, for example a single or recurring dose on a daily, weekly or monthly basis, for example orally.

In a particular embodiment, the composition according to the present invention is administered to a high-risk group of people.

In a particular embodiment, the composition according to the present invention is administered to a population of age greater than or equal to 40 years, greater than or equal to 50 years, greater than or equal to 60 years, greater than or equal to 70 years, greater than or equal to 80 years or greater than or equal to 90 years.

EXAMPLES

Example 1: Composition and Toxicity

An embodiment of the present invention will be described hereinafter, by way of non-limiting example.

An example of a composition fitting into the configuration explained in the above claims is summarized in the following table.

TABLE 2

Composition Made

| COMPOSITION | GRAMS |
|---|---|
| SPEARMINT ESSENTIAL OIL | 0.08 |
| MENTHOL | 0.09 |
| WATER MINT ESSENTIAL OIL | 0.07 |
| CLOVE ESSENTIAL OIL | 0.06 |
| PEPPERMINT ESSENTIAL OIL | 0.07 |
| PENNYROYAL ESSENTIAL OIL | 0.06 |
| EUCALYPTUS ESSENTIAL OIL | 0.16 |
| CINNAMON ESSENTIAL OIL | 0.06 |
| cajuput ESSENTIAL OIL | 0.08 |
| CAMPHOR | 0.27 |
| QSP SESAME OIL | 9 |

In addition, the levels of the various constituents were measured:

- the spearmint essential oil as used comprised 40.8% carvone and 20.8% limonene;
- the menthol as used comprised 100% menthol;
- the water mint essential oil as used comprised 12.06% limonene, 51.26% menthofuran, 8.1% ocimene and 2.92% beta-caryophyllene;
- the clove essential oil as used comprised 76.8% eugenol, 17.4% beta-caryophyllene, 2.1% alpha-humulene, 1.2% acetyleugenol;
- the peppermint essential oil as used comprised 39.81% menthol, 19.55% menthone, 5.81%1,8-cineole, 8.83% neomenthol and 8.64% menthyl acetate;
- the pennyroyal essential oil as used comprised 35.9% menthol, 23.2% pulegone, 9.2% neomenthol;
- the eucalyptus essential oil as used comprised 80.51% limonene, 8.6% alpha-terpineol, 6.07% alpha-terpinyl acetate, 3.01% alpha-pinene;
- the cinnamon essential oil as used comprised 5.8% eugenol, 2.6% alpha-pinene, 76.8% cinnamaldehyde, 3.1% cinnamyl acetate, 2.4% linalool;
- the cajuput essential oil as used comprised 21.3%1,8-cineole, 28.2% viridiflorol;
- the camphor as used comprised 30.02%1,8-cineole, 5.22% alpha-terpineol, 36.61% camphor and 5.15% safrole; and
- the sesame oil as used comprised 41% linoleic acid, 39% oleic acid, 8% palmitic acid and 5% stearic acid.

At the levels indicated in tables 1 and 2, all of the active ingredients mentioned above are below their LD50 threshold, confirming that the solution does not exhibit any particular toxic effect.

Example 2: In Vivo Test 19 patients infected with Sars-CoV-2 or presenting pathological symptoms of Sars-CoV-2 (1 patient not having been PCR tested) took the composition according to Example 1 during the Sars-CoV-2 pandemic. All these volunteers were informed under confidentiality agreement of the general content of the composition and of the possibly incurred risks (which are minimal given the toxicological profile of the composition). None of the volunteers were vaccinated.

The average age was 40 at the time of the tests with the oldest person being 77 years old and the youngest person being 27 years old. After taking the composition (a single dose), none of the people developed a severe form of the disease. All were able to see an improvement in their condition. However, one patient presented persistent anosmia, the only symptom that persisted in his case, and another presented partial anosmia. No other patient presented any other post-infection symptoms known as "long covid". All the patients were then free to summarize, in a medical testimony statement, the description of their own state of health before and after administration of the composition according to Example 1.

TABLE 3

Table 3 summarizes some aspects of the performed test and the obtained results:

| Number of patients | Age range (years) | Average age per range (years) | Persistent negative effects after treatment | Improvement: time observed until first improvement after administration, if specified | | | |
|---|---|---|---|---|---|---|---|
| | | | | 0-24 h | 24 h-48 h | 72 h and more | Unspecified |
| 14 | 20-40 | 37 | 1 (anosmia) | 1 | 1 | 1 | 11 |
| 3 | 40-60 | 50 | 1 (partial anosmia) | 1 | 0 | 1 | 1 |
| 2 | 60-80 | 69 | 0 | 1 | 0 | 0 | 1 |

Several of the patients noticed by themselves a very rapid improvement in their condition and pointed it out. This test therefore seems to show a beneficial activity of the composition according to the present invention, given that the most serious symptoms (cough, difficulty in breathing, fever, etc.) disappeared for all patients who took the composition according to the invention. Only one of the two patients retained anosmia as a symptom, one of which was partial, which is not a lethal or highly incapacitating symptom in the long term.

The invention claimed is:

1. A therapeutic composition comprising a mixture of essential oils for the use thereof in treating at least one respiratory infection by oral administration, said mixture of essential oils including a spearmint essential oil, menthol, a water mint essential oil, a clove essential oil, a peppermint essential oil, a pennyroyal essential oil, a eucalyptus essential oil, a cinnamon essential oil, a cajuput essential oil, and camphor characterized in that said composition includes between 0.04 and 0.08 grams of a spearmint essential oil, between 0.05 and 0.09 grams of menthol, between 0.03 and 0.07 grams of a water mint essential oil, between 0.02 and 0.06 grams of a clove essential oil, between 0.03 and 0.07 grams of a peppermint essential oil, between 0.02 and 0.06 grams of a pennyroyal essential oil, between 0.12 and 0.16 grams of a eucalyptus essential oil, between 0.02 and 0.06 grams of a cinnamon essential oil, between 0.04 and 0.08 grams of a cajuput essential oil, and between 0.23 and 0.27 grams of camphor, and between 4 and 9 grams of edible vegetable oil as an excipient.

2. The therapeutic composition according to claim 1, characterized in that said composition further comprises at least one edible vegetable oil as an excipient.

3. The therapeutic composition according to claim 2, characterized in that the excipient is selected from sesame oil, olive oil or a mixture thereof.

4. The therapeutic composition according to claim 1, characterized in that said composition comprises between 4 grams and 9 grams of excipient.

5. The therapeutic composition according to claim 1, characterized in that said composition is in the form of an ampoule.

6. The therapeutic composition according to claim 1, characterized in that said composition comprises between 0.60 grams and 1.0 grams of a mixture of essential oils.

7. The therapeutic composition according to claim 1, characterized in that said composition includes 0.08 grams of a spearmint essential oil, 0.09 grams of menthol, 0.07 grams of a water mint essential oil, 0.06 grams of a clove essential oil, 0.07 grams of a peppermint essential oil, 0.06 grams of a pennyroyal essential oil, 0.16 grams of a eucalyptus essential oil, 0.06 grams of a cinnamon essential oil, 0.08 grams of a cajuput essential oil, and/or 0.27 grams of camphor and optionally 9 grams of edible vegetable oil as an excipient.

8. The therapeutic composition according to claim 1, characterized in that the excipient is selected from sesame oil, olive oil or a mixture thereof.

9. The therapeutic composition according to claim 1, characterized in that the respiratory infection is selected from influenza, and common cold, bronchitis a pneumopathy.

10. A therapeutic composition in the form of an ampoule with a volume of five milliliters to ten milliliters comprising essential oils at low doses and intended for oral use, in the form of a mixture, and an excipient comprising at least one edible vegetable oil, said mixture including a spearmint essential oil, menthol, a water mint essential oil, a clove essential oil, a peppermint essential oil, a pennyroyal essential oil, a eucalyptus essential oil, a cinnamon essential oil, a cajuput essential oil, and camphor characterized in that said essential oil mixture includes between 0.04 and 0.08 grams of a spearmint essential oil, between 0.05 and 0.09 grams of menthol, between 0.03 and 0.07 grams of a water mint essential oil, between 0.02 and 0.06 grams of a clove essential oil, between 0.03 and 0.07 grams of a peppermint essential oil, between 0.02 and 0.06 grams of a pennyroyal essential oil, between 0.12 and 0.16 grams of a eucalyptus essential oil, between 0.02 and 0.06 grams of a cinnamon essential oil, between 0.04 and 0.08 grams of a cajuput essential oil, and between 0.23 and 0.27 grams of camphor.

11. The therapeutic composition according to claim 10, characterized in that the excipient is sesame oil or olive oil.

12. The therapeutic composition according to claim 10, characterized in that the mixture of essential oils contains between 250 milligrams and 1 gram, or between 0.6 grams and 1.0 gram of essential oils at low doses.

13. The therapeutic composition according to claim 10, comprising 0.08 grams of a spearmint essential oil, 0.09 grams of menthol, 0.07 grams of a water mint essential oil, 0.06 grams of a clove essential oil, 0.07 grams of a peppermint essential oil, 0.06 grams of a pennyroyal essential oil, 0.16 grams of a eucalyptus essential oil, 0.06 grams of a cinnamon essential oil, 0.08 grams of a cajuput essential oil, 0.27 grams of camphor, and 9 grams of sesame oil.

14. The therapeutic composition according to claim 10, for treating influenza, acute bronchitis.

15. The therapeutic composition according to claim 1, characterized in that the camphor is in crystals or as a camphor essential oil.

16. The therapeutic composition according to claim 9, characterized in that the pneumopathy is a viral pneumonia or a Sars-CoV-2 pneumopathy.

* * * * *